(12) United States Patent
Karjalainen

(10) Patent No.: US 8,054,176 B2
(45) Date of Patent: Nov. 8, 2011

(54) PERFORMANCE MONITOR, TRANSMISSION METHOD AND COMPUTER PROGRAM PRODUCT

(75) Inventor: Markku Karjalainen, Kempele (FI)

(73) Assignee: Polar Electro Oy, Kempele (FI)

( * ) Notice: Subject to any disclaimer, the term of this patent is extended or adjusted under 35 U.S.C. 154(b) by 611 days.

(21) Appl. No.: 12/133,888

(22) Filed: Jun. 5, 2008

(65) Prior Publication Data

US 2009/0009342 A1   Jan. 8, 2009

(30) Foreign Application Priority Data

Jun. 8, 2007  (FI) ...................................... 20075426

(51) Int. Cl.
 *G08B 1/08* (2006.01)
(52) U.S. Cl. ........... 340/539.12; 340/539.11; 340/573.1; 340/323 R; 128/696; 128/903; 482/8; 600/300; 600/382
(58) Field of Classification Search ............ 340/539.11–539.12, 870.3, 323 R, 573.1; 600/300–306, 600/509–514, 374–384; 128/201.27, 901–904; 482/8–9; 702/19, 160; 706/54; 726/28; 379/201.05; 455/66.1, 100; 434/238
 See application file for complete search history.

(56) References Cited

U.S. PATENT DOCUMENTS

| | | | | |
|---|---|---|---|---|
| 5,458,122 A * | 10/1995 | Hethuin | ........................ | 600/509 |
| 5,690,119 A | 11/1997 | Rytky et al. | | |
| 6,093,146 A * | 7/2000 | Filangeri | ........................ | 600/300 |
| 6,185,525 B1 * | 2/2001 | Taubenheim et al. | ......... | 704/211 |
| 6,436,052 B1 | 8/2002 | Nikolic et al. | | |
| 7,177,672 B2 | 2/2007 | Nissila | | |
| 7,771,320 B2 * | 8/2010 | Riley et al. | ........................ | 482/9 |
| 2002/0007126 A1 | 1/2002 | Nissila | | |
| 2002/0042266 A1 * | 4/2002 | Heyward et al. | .............. | 455/414 |
| 2003/0130708 A1 | 7/2003 | Von Arx et al. | | |
| 2003/0163287 A1 | 8/2003 | Vock et al. | | |
| 2003/0167079 A1 | 9/2003 | Birnbaum et al. | | |
| 2004/0260463 A1 | 12/2004 | Hathiram et al. | | |
| 2006/0135863 A1 * | 6/2006 | Birnbaum et al. | ............ | 600/388 |
| 2006/0264767 A1 | 11/2006 | Shennib | | |
| 2007/0015973 A1 * | 1/2007 | Nanikashvili | ................. | 600/300 |

FOREIGN PATENT DOCUMENTS

| | | |
|---|---|---|
| EP | 0892731 B9 | 10/2004 |
| FI | 111215 B | 6/2003 |
| FI | 117885 B | 4/2007 |
| WO | WO0100281 A2 | 1/2001 |
| WO | WO2005084533 A1 | 9/2005 |
| WO | WO2008032315 A1 | 3/2008 |

OTHER PUBLICATIONS

Raphael Kronberger, Extended European Search Report for corresponding European application EP 08157710.8, pp. 1-4 (Aug. 3, 2011).

* cited by examiner

*Primary Examiner* — Brent Swarthout

(74) *Attorney, Agent, or Firm* — Hoffmann & Baron, LLP

(57) ABSTRACT

A data transmission method for use in the transmission of a performance transmitter of a portable user-specific performance monitor by using wireless data transmission that is based on radio-frequency electromagnetic radiation, and the method comprises measuring with the performance monitor the movement and/or organ system state of a user. In the solution, the availability of wireless data transmission in the performance transmitter is determined. If wireless data transmission is not available, measuring data is stored into a memory of the performance transmitter, otherwise the measuring data is transmitted using wireless data transmission.

14 Claims, 4 Drawing Sheets

PERFORMANCE MONITOR, TRANSMISSION METHOD AND COMPUTER PROGRAM PRODUCT

CROSS-REFERENCE TO RELATED APPLICATION

This application claims priority based on Finnish Patent Application No. 20075426, filed Jun. 8, 2007, which is incorporated herein by reference.

BACKGROUND OF THE INVENTION

1. Field of the Invention

The invention relates to a portable user-specific performance monitor and a related transmission method and computer program product.

2. Description of the Related Art

It is important to measure the functioning of the organ system and the movement of a person when training for an athletic performance, for example. The heart rate of a person can be measured with a portable device that comprises a measuring belt fastened on the chest with an elastic belt and a heart rate receiver fastened on the wrist like a watch which serves as a receiver of measuring data and may process the measuring data.

The measuring belt consists of a flexible piece fastened on the chest with a sensor for measuring an ECG signal. The sensor comprises two measuring electrodes that settle against the skin and are connected to an ECG detecting block. Instead of ECG measurement or in addition to it, it is possible to use other sensors to measure the state of the organ system or movement of the user. These include acceleration sensors that provide information on the movements of the user.

A transmitter in the measuring belt or some other sensor may wirelessly transmit measuring data by means of radio-frequency electromagnetic radiation to the measuring data receiver fastened to the wrist of a user for processing therein. From the measuring belt or wrist receiver, the measuring data may be transmitted on to a computer or some other corresponding receiver for further processing.

However, there are problems associated with data transmission by means of radio-frequency electromagnetic radiation. If the measuring data transmitter or receiver is in sufficiently humid conditions, for instance when the user goes swimming, radio-frequency electromagnetic radiation cannot propagate through water from the transmitter to the receiver. Sometimes the fact that the transmitter is too far from the receiver prevents data transmission. It is also possible that the user is in an environment where the operation of a transmitter is not allowed. The measuring data generated during a break in the data transmission then cannot be processed in the receiver and the measuring data thus cannot be used for an analysis of the performance of the user.

SUMMARY OF THE INVENTION

It is an object of the invention to implement an improved transmission method for a performance monitor. This is achieved by a data transmission method that is used in the transmission of a portable user-specific performance monitor by employing wireless data transmission that is based on radio-frequency electromagnetic radiation, the method comprising measuring with a performance monitor the movement and/or organ system state of the user. The method further comprises detecting whether wireless data transmission of the performance monitor is available, and storing measuring data into the memory of the performance monitor, if wireless data transmission is not available, otherwise transmitting the measuring data using wireless data transmission.

The invention also relates to a portable user-specific performance monitor that comprises a performance transmitter, the performance monitor being configured to measure the movement and/or organ system state of the user and to transmit the measuring data wirelessly using radio-frequency electromagnetic radiation. The performance transmitter comprises a memory and is configured to detect the availability of wireless data transmission, to store measuring data into the memory of the performance transmitter when it detects that wireless data transmission is not available to it, and to transmit the measuring data stored in its memory when the performance monitor detects that wireless data transmission is available.

The invention further relates to a computer program product that contains encoded instructions that when loaded into a portable user-specific performance monitor form a computer process that controls the transmission operations of the performance monitor transmitter, when the performance monitor is arranged to measure the movement and/or organ system state of the user and to transmit the measuring data wirelessly using radio-frequency electromagnetic radiation. The computer process comprises detecting the availability of wireless transmission of the performance transmitter and storing measuring data into the memory of the performance transmitter if wireless transmission is not available, otherwise directing the performance transmitter to transmit measuring data using wireless transmission.

Preferred embodiments of the invention are disclosed in the dependent claims.

The method and system of the invention provide several advantages. Measuring data is not lost during connection breaks, but a connection break can be detected and measuring results stored while it lasts. The stored measuring results can be transmitted after the connection break to the communication device serving as the receiver.

BRIEF DESCRIPTION OF THE DRAWINGS

The invention will now be described in greater detail by means of preferred embodiments and with reference to the attached drawings, in which.

DETAILED DESCRIPTION OF THE PREFERRED EMBODIMENTS

Figure 1:
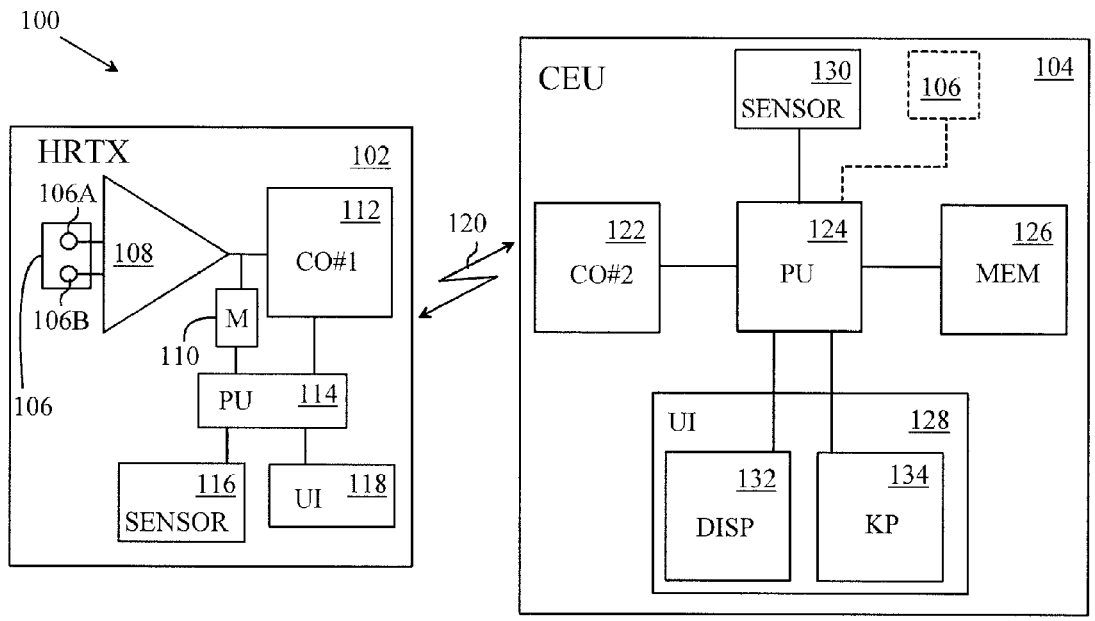
FIG. 1 shows a block diagram of the performance monitor.

FIG. 1 shows an example of a block diagram of the portable user-specific performance monitor 100. In this context, the user-specific performance monitor is referred to as performance monitor. The performance monitor 100 may comprise a measuring unit 102 and a main unit 104. The measuring unit 102 may be a performance transmitter and one possible communication device to which it transmits its signal is the main unit 104. The measuring unit 102 may comprise one or more sensors 106 measuring movement or state of the organ system, a pre-amplifier 108, buffer memory 110, and communication unit (CO#1) 112. In addition, the measuring unit 102 may comprise a processing unit 114, environment sensor 116, and user interface 118.

The main unit 104 may comprise a communication unit (CO#2) 122, processing unit (PU) 124, memory unit (MEM), and a user interface (UI) 128. In addition, the main unit 104 may comprise an environment sensor 130. The main unit 104 may also comprise one or more sensors 106 that measure movement or state of the organ system, whereby the main unit 104 may also serve as a performance transmitter.

The sensor 106 may measure the state of the organ system or the movement of the user. Heart beat, amount of inhaled air, respiratory frequency, blood pressure, oxygen content in blood, etc. may represent the state of the organ system. From the movement of the user, it is possible to measure style, efficiency, or distance, for instance.

For instance, when measuring heart beat, electrodes 106A, 106B of the sensor 106 may indicate the voltage generated by the electric activity of the heart and produce an ECG (Electrocardiogram) signal that depicts the electric activity of the heart. The ECG signal may be input from the electrodes 106A, 106B to the ECG pre-amplifier 108 that may contain several amplification levels. ECG information may be processed in such a manner that it contains the ECG as such, part of the ECG and/or timing information of heart beat. The timing information may contain a timing pulse that represents a predefined part of the ECG.

One or more of the sensors 106 may be magnetic or acceleration sensors when measuring the movement of the user during sports performance or training, for instance (see FIG. 5).

The pre-amplifier 108 amplifies the measuring signal and inputs the amplified signal through the buffer memory 110 to the communication unit 112.

The processing unit 114, which may process the signal to be stored into the memory 110 and/or the signal to be transferred from the memory 110 to the communication unit 110, may be implemented using analogue circuits, ASIC (application-specific integrated circuit), a digital processor, memory, and computer software. The processing unit 114 may form part of the computer of the performance monitor 100.

The communication unit 112 may contain several consecutive amplification levels, such as an AGC (automatic gain control) amplifier and power amplifier. The communication unit 112 generates a signal 114 transferring measuring data and communicates through wireless data transmission. The measuring unit 102 may also be a transceiver, in which case the communication unit 112 may receive radio-frequency electromagnetic radiation transmitted by the main unit 104 or some other predefined communication device.

The measuring unit 102 may also comprise one or more environment sensors 116 that may measure for instance whether the user is in water or not. The environment sensor 116 may measure an electric property, pressure, height, or the like.

A communication unit 122 of the main unit 104 may receive a signal 120 transferring measuring data and input the measuring data into a processing unit 124 that executes a computer process according to encoded instructions stored in a memory unit 126.

The processing unit 124 may be implemented using analogue circuits, ASICs (application-specific integrated circuit), a digital processor, memory, and computer software. The processing unit 124 may form part of the computer of the performance monitor 100.

A user interface 128 may contain a display (DISP) 132 and display controller. The display 132 may be an LCD (liquid crystal display) display, for example. The display 132 may show graphical and/or numerical measuring data and performance instructions to the user.

The user interface 128 may also comprise a keypad (KP) 134 with which the user may input commands to the performance monitor 100.

The main unit 104 may also comprise one or more environment sensors 130 that may measure for instance whether the user is in water or not. The one or more environment sensors may measure an electric property, pressure, height, or the like.

The measuring unit 102 makes measurements and transmits the measuring data to the main unit 104, for instance. In some embodiments measuring heart beat, the measuring unit 102 may contain a heart beat detector that detects a predefined portion of ECG, generates measuring data representing the timing of the predefined portion of ECG and transmits the measuring data to the main unit 104 or to some other predefined communication device.

The main unit 104 typically contains device parts 122 to 134 that process the signal 120 transmitting measuring data and the measuring data and implement the user interface.

In one embodiment, the measuring unit 102 and main unit 104 may be integrated into the same performance monitor 100, whereby a performance monitor is formed which is fastened to the wrist or to the handlebar of a bicycle. The integrated performance monitor acts as a performance transmitter, because it can transmit measuring data wirelessly by employing radio-frequency electromagnetic radiation to a predefined communication device. In such a case, some of the device parts shown in FIG. 1, such as the communication unit 122 of the main unit, may not be necessary, but one communication unit can be used that is similar to the communication unit 112 and may communicate with a predefined communication device in the environment (see FIG. 3).

Figure 2:
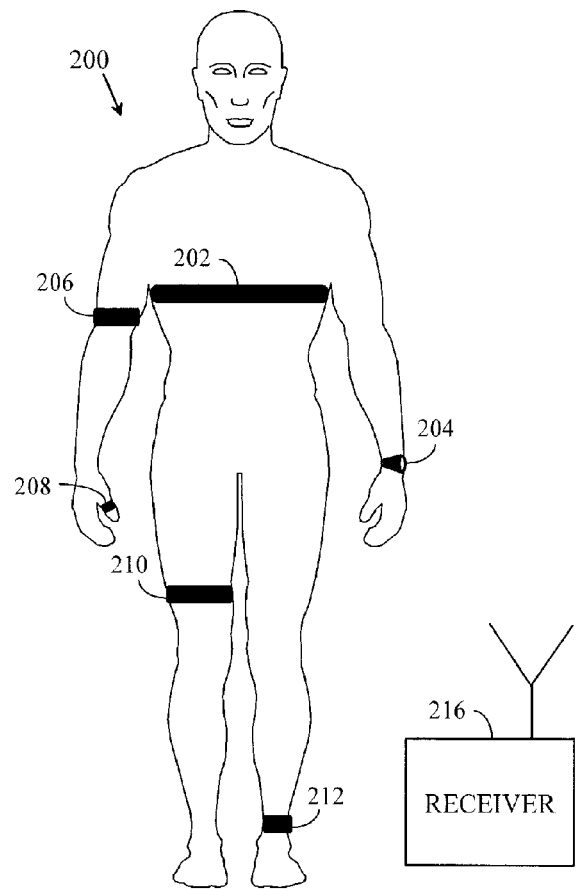
FIG. 2 shows a user wearing the performance monitor.

With reference to the embodiment shown in FIG. 2, the measuring transmitter 102 may be a transmitter belt 202 that can be fastened around the chest of a user 200. ECG data may be transmitted as radio-frequency electromagnetic radiation from the transmitter belt 202 to a receiver 204 that may be the main unit 104 and fastened to the wrist or to a bicycle. FIG. 2 shows the user 200 wearing several other performance transmitters 206 to 212 which may contain acceleration sensors, for example. Each performance transmitter 202 to 212 measures the movement and/or organ system state of the user and transmits measuring data to a predefined communication device that may be a wrist device 204 or a communication device 216 in the environment. The acceleration sensors may for instance determine the pace, acceleration, efficiency and/or possibly style of the user's movements.

For instance, in triathlon, the first sport is swimming, followed by bicycling and running. Because wireless data transmission between the transmitter belt 202 acting as the performance transmitter and the wrist device 204 does not work during swimming, the user may have the wrist device 204 and transmitter belt 202 or only the transmitter belt 202 during swimming. When the user approaches the bicycle equipped with the main unit 104, s/he is no longer in water or too far from the main unit 104 acting as a receiver. The transmitter belt 202 can then transmit the stored measuring data to the main unit 104 on the user or on the bicycle for instance. The main unit receiving the data may display to the user information related to the swimming and guide the bicycling on the basis of the information. In addition, one or more sensors in the bicycle transmit measuring data during bicycling to the main unit 104 used by the user. The data transmission may be secured in that data is only transmitted to the desired main unit.

The main unit 104 may also contain a performance transmitter that measures a movement and/or organ system state of the user. The performance transmitter in the main unit 104 may then transmit measuring data to a predefined communication device in the environment.

In one embodiment the measuring unit 102 and part of the main unit 104 are integrated to the transmitter belt 202, whereby the transmitter belt 202 can collect ECG data, process it and define values for quantities characterizing the heart beat. The signal 120 transferring ECG information may then transmit processed information, such as values of quantities characterizing the heart beat and commands given by the user, between the transmitter belt 202 and wrist device 204 or some other predefined communication device.

Figure 3:
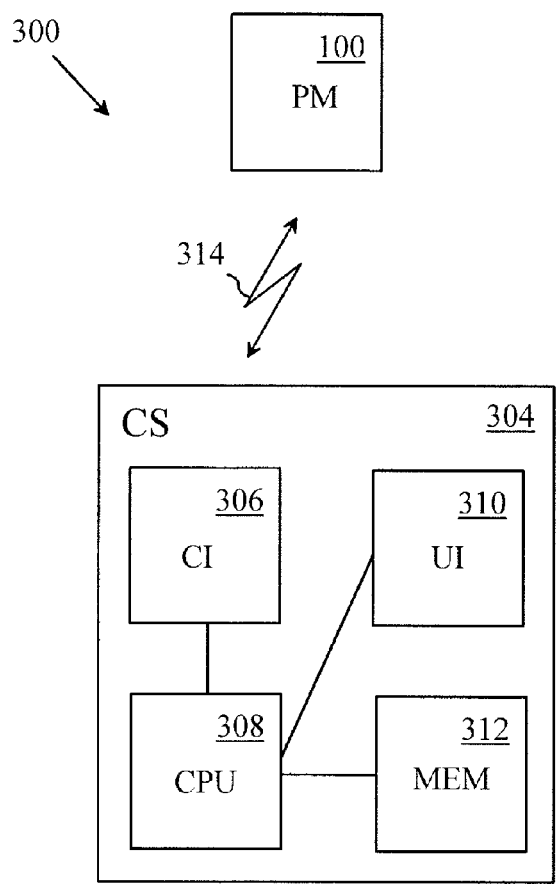
FIG. 3 shows wireless data transmission to a communication device in the surroundings.

With reference to the example of FIG. 3, the system 300 may comprise a performance monitor (PM) 100 and a data collection unit (CS) 304 that acts as the predefined communication device and may correspond to the communication device 216 of FIG. 2. The data collection unit 304 may be used in a gym, for instance.

The data collection unit 304 may comprise a communication interface (CI) 306, central processing unit (CPU) 308, memory unit (MEM) 312, and user interface 310. The performance monitor 100 may transmit measuring data in a signal 314 through the communication interface 306 to the data collection unit 304.

The communication interface 306 that operates wirelessly through radio-frequency electromagnetic radiation is capable of receiving and possibly also transmitting.

During a gym exercise the performance monitor 100 stores measuring data into the memory 110, 126, because the performance monitor 100 may for instance be too far from the data collection unit 304 acting as a receiver or the user has prevented the use of wireless data transmission during the exercise. The performance monitor 100 may transmit measuring data to the data collection unit 304 for instance when the user exits the gym. At the door of the gym there may be a communication interface 306 that receives measuring data stored into the memory of each performance monitor passing through the door.

The central processing unit 308 may execute a computer process according to encoded instructions stored in the memory unit 312 for displaying the measuring data and/or generating performance instructions. The central processing unit 308 may input the results of the processing to the user interface 310.

A calculation system 304 may be implemented by means of a computer and software, for instance. The communication interface 306 may be integrated to the calculation system, or it may be a peripheral device connectable to the calculation system. If the communication interface 306 is a peripheral device, the communication interface 306 may also operate independently as the predefined communication device.

Figure 4:
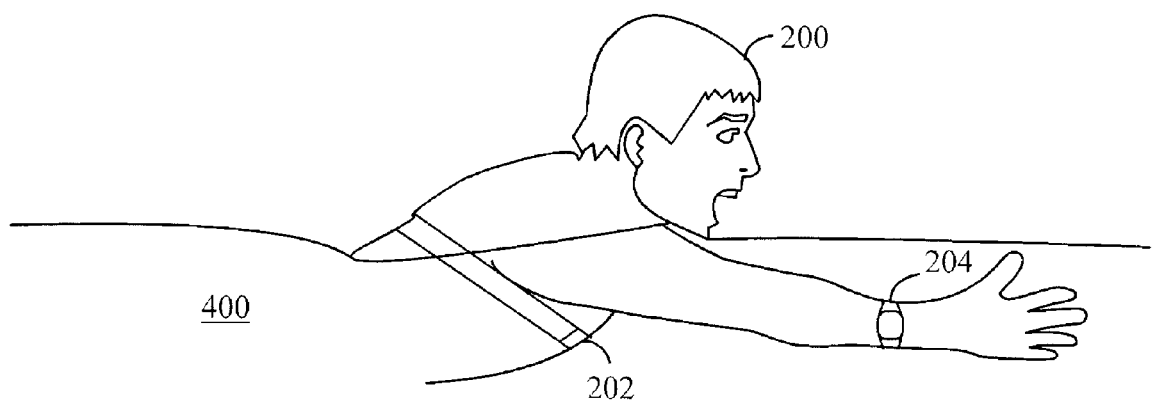
FIG. 4 shows a user swimming.

FIG. 4 shows the user 200 swimming. Both the transmitter belt 202 and the wrist device 204 may then be under water 400, in which case the radio-frequency electromagnetic wireless data transmission between them is not possible. The wrist device 204 may at times be above water and especially in backstroke the actual measuring and transmitter part of the transmitter belt 202 may also be above water at least occasionally. But since data transmission is uncertain, the user may for instance before going into the water prevent wireless transmission by giving an inhibiting command through the user interface. When the user 200 gets out of the water, he may again allow data transmission by giving a permit command through the user interface. If the user does not give any command through the user interface, the sensor of the wrist device 204 or the sensor of the transmitter belt 202 may detect that the user is in water 400 and prevent data transmission. Correspondingly, data transmission may be permitted when the sensor detects that the transmitter belt 202 and wrist device 204 are no longer in water 400. The transmitter belt 202 may also at intervals transmit a signal to be acknowledged to the wrist device 204, and if the transmitter belt 202 does not receive an acknowledgement signal from the wrist device 204, it may continue transmitting the same signal to be acknowledged or end data transmission for a predefined time before re-sending the signal to be acknowledged. When the acknowledgement signal is received, data transmission can again be continued. In packet-switched data transmission, each packet is acknowledged received. When among consecutive packets $p_1$ to $P_i$, wherein n is an integer larger than 1, a packet $p_i$, wherein i obtains the value $1 \leq i \leq n$, does not immediately receive an acknowledgement, the packet $p_i$ is retransmitted until its receipt is acknowledged.

Let us now examine more closely the transmission of measuring data from the performance transmitter. When starting the transmission or during it, the performance transmitter may detect whether wireless data transmission is available. In this application, wireless data transmission refers to radio-frequency electromagnetic radiation that propagates in the air. Wireless data transmission may operate on a frequency above 100 kHz, for instance. One possible operating frequency is approximately 2.4 GHz. The availability of wireless data transmission may mean that wireless data transmission cannot be used or can be used. The default can be that data transmission is available if nothing has been detected that indicates that it is not available.

In general, the performance transmitter may detect something with which the availability of data transmission can be ascertained and control data transmission according to the availability. What is detected may be a property of the environment, a command, the arrival of a signal within the time allocated for reception or the lack of it, etc.

The availability of wireless data transmission may be detected from a signal of the user interface 118 or environment sensor 116, 130. In addition, the performance transmitter may receive from a predefined communication device, such as the main unit 104, a signal that defines the availability of wireless data transmission.

The user may use the keyboard of the user interface 118 to form an inhibiting command that prohibits wireless data transmission and a permit command that enables wireless data transmission. The user interface 118 may have one button that when pressed enables or prohibits wireless data transmission. The user interface 118 may comprise an alphanumeric keyboard with which the desired command may be input into the measuring unit 102. The user interface 118 may also be speech-controlled, in which case the command can be received as speech.

The environment sensor 116, 130 may reside in the measuring unit 102 or main unit 104. The environment sensor may be a resistive sensor, capacitive sensor, altimeter, hygrometer or the like. If the environment sensor is at the measuring unit 102 (like the environment sensor 116), it may supply its measuring results to the processing unit 114 or communication unit 112 that detects the availability of wireless data transmission on the basis of the signal of the environment sensor 116, 130. The processing unit 114 may then control the communication unit 112 according to the measuring result of the environment sensor or the communication unit 112 may directly operate according to the measuring result of the environment sensor. The environment sensor may also be provided with a threshold value in such a manner that it does not supply the measuring value but supplies an on/off-type signal on the state of wireless data transmission. The environment sensor then does not supply a signal when the state of the environment permits the use of wireless data transmission. But when the state of the environment prohibits the use of wireless data transmission, the environment sensor supplies a desired signal. It is also possible that the environment sensor supplies a different signal when wireless data transmission is available than when it is not.

A resistive sensor may measure the resistance between two or more electrodes. The sensor may transmit to the performance transmitter a measuring signal of the resistance value that may define the availability of wireless data transmission. When the resistance is lower than a predefined threshold value, the environment sensor 116, 130 transmits to the processing unit 114 or communication unit 112 of the measuring unit 102 a measuring signal. On the basis of this, the processing unit 114 or communication unit 112 may detect whether wireless data transmission is available. The measuring result of the environment sensor may be compared with a threshold value having values on one side depict that wireless data transmission is available and on the other side that it is not. The threshold value may be selected to belong to either side. If wireless data transmission is not available, the measuring unit 102 does not transmit or interrupts the already started wireless transmission and starts to store the measuring data into the memory 110. For instance, in water the resistance is lower than in air.

The environment sensor 116, 130 may also be a capacitive sensor that measures the capacitance between two or more electrodes. A change in the relative dielectric constant of a medium between electrodes also changes the capacitance between the electrodes. For instance, the relative dielectric constant of water is higher than that of air, which means that a capacitive sensor detects the increase in capacitance when the sensor moves from air to water. Correspondingly, the capacitance decreases strongly when moving from water to air. The environment sensor may signal to the performance transmitter the capacitance value with which the availability of wireless data transmission can be detected. A threshold value can then be set for the capacitance, and when the value is exceeded, it indicates that wireless data transmission is not available. The threshold value and a value below it may indicate that wireless data transmission is available.

If the environment sensor 116, 130 is an altimeter, the sensor measures elevation above ground. The measurement is often made as air pressure measurement. Because the density of water, for instance, is higher than that of air, pressure measurement can be used to easily detect the movement of the performance transmitter from air to water and vice versa. When the pressure meter detects a pressure higher than that of a predefined threshold value or a pressure increase, this can be thought to mean that the performance meter has moved from air to water and that wireless data transmission is not available. Correspondingly, when the pressure meter detects a pressure smaller than that of the predefined threshold value or a pressure decrease, this can be thought to mean that the performance meter has moved from water to air and that wireless data transmission is available.

When the environment sensor 116, 130 is a hygrometer, the difference between water and air is easy to detect. If the humidity measured by the hygrometer exceeds a predefined threshold, which may for instance be the highest humidity value of the hygrometer or some other suitable value, it can be assumed that the hygrometer and thus also the performance transmitter is in water, which means that wireless data transmission is not available. Detecting a humidity value that is the same or below the threshold value in turn means that wireless data transmission is available. In addition to being in water, the user may be in a watery environment, for instance s/he may be wearing a wet suit that has absorbed a lot of water. If the performance transmitter is against the user's skin under the wet suit, the hygrometer may find that the humidity is too high for successful wireless data transmission. This way, it is possible to detect from the hygrometer signal that wireless data transmission is not available.

Each environment sensor may input into the processing unit 114 or communication unit 112 of the performance transmitter a measuring signal with which the processing unit 114 or communication unit 112 detects the availability of wireless data transmission. Each environment sensor may also process the measuring signal and detect whether wireless data transmission is available. Each environment sensor then signals the determined result to the processing unit 114 or communication unit 112.

Instead of a sensor a predefined communication device 104, 304 that comprises one or more sensors 116, 130 of the type described above may also prevent wireless data transmission. The reason may be, for instance, that the predefined communication device 104, 304 is damaged, the memory is full, the distance is too long, or the meter is in water, etc. The performance transmitter (measuring unit 102) may then receive from the predefined communication device 104, 304 a signal that comprises a transmission-inhibiting command. Direct detection of the inhibiting command defines that wireless data transmission is not available. The fact that an acknowledgement for a signal to be acknowledged is not received from the predefined communication device 104, 304, but the lack of the signal is detected, also indicates to the performance transmitter that wireless data transmission is not available. The predefined communication device 104, 304 may send a wireless data transmission permit command when reception at the predefined communication device 104, 304 is again possible.

When the performance transmitter (e.g. measuring unit 102) has received a signal by means of which it is possible to detect that wireless data transmission is not available to the performance transmitter, the performance transmitter does not transmit any measuring data but stores it into its memory (e.g. the memory 110 of the measuring unit 102).

When the performance transmitter (e.g. measuring unit 102) receives a signal by means of which it is possible to detect that wireless transmission is available or again available, the performance transmitter transmits data stored in its memory (e.g. memory 110 of the measuring unit 102). When the measuring data stored in the memory has been transmitted, the performance transmitter may continue the direct transmission of the measuring data or stop the transmission, if measuring is no longer done. The receiver of the transmission may be the main unit 104 or some other predefined communication device 304.

Measuring and transmission activity may already be ongoing in the performance monitor when it detects that wireless transmission is not available. It then begins to store measuring data into its memory.

The performance transmitter may also actively test whether wireless data transmission is available. The performance transmitter (e.g. measuring unit 102) then transmits a signal to which the predefined communication device 104, 304 must transmit an acknowledgement signal. The performance transmitter waits for a predefined delay time for the acknowledgement and then detects that wireless data transmission is not available if no acknowledgement signal arrives within the predefined time. The performance transmitter then begins to store measuring data into the memory. If the acknowledgement signal arrives in time, its detection indicates that wireless data transmission is available. The performance transmitter may then transmit measuring data wirelessly. The signal to be acknowledged may be transmitted regularly to monitor the success of reception.

If the storing into the memory continues a long time, it is possible that the memory begins to fill up and its capacity is at risk of exceeding. The performance transmitter may then compress the measuring data being stored into its memory. Compression may be started if the degree of full-ness of the memory exceeds a predefined threshold value that may be approximately 80% of the total capacity of the memory. Compression may further be boosted in such a manner that the performance transmitter may compress both the measuring data to be stored into the memory and the measuring data already in the memory.

Compression may be done for instance by averaging the measuring data. Initially the measuring result may be stored as such. For example, each piece of heart beat information may be stored in this manner. If compression is needed, the measuring results may be averaged for a period of a few seconds, for instance. It is then possible to store 5-second averaged heart beat information, for instance. If there is still a risk of exceeding memory capacity, the averaging time may be lengthened by averaging measuring results for a period of 10 seconds, for instance. This may be continued until the performance transmitter is again able to transmit measuring data and upload the measuring data stored into the memory.

Figure 5A:
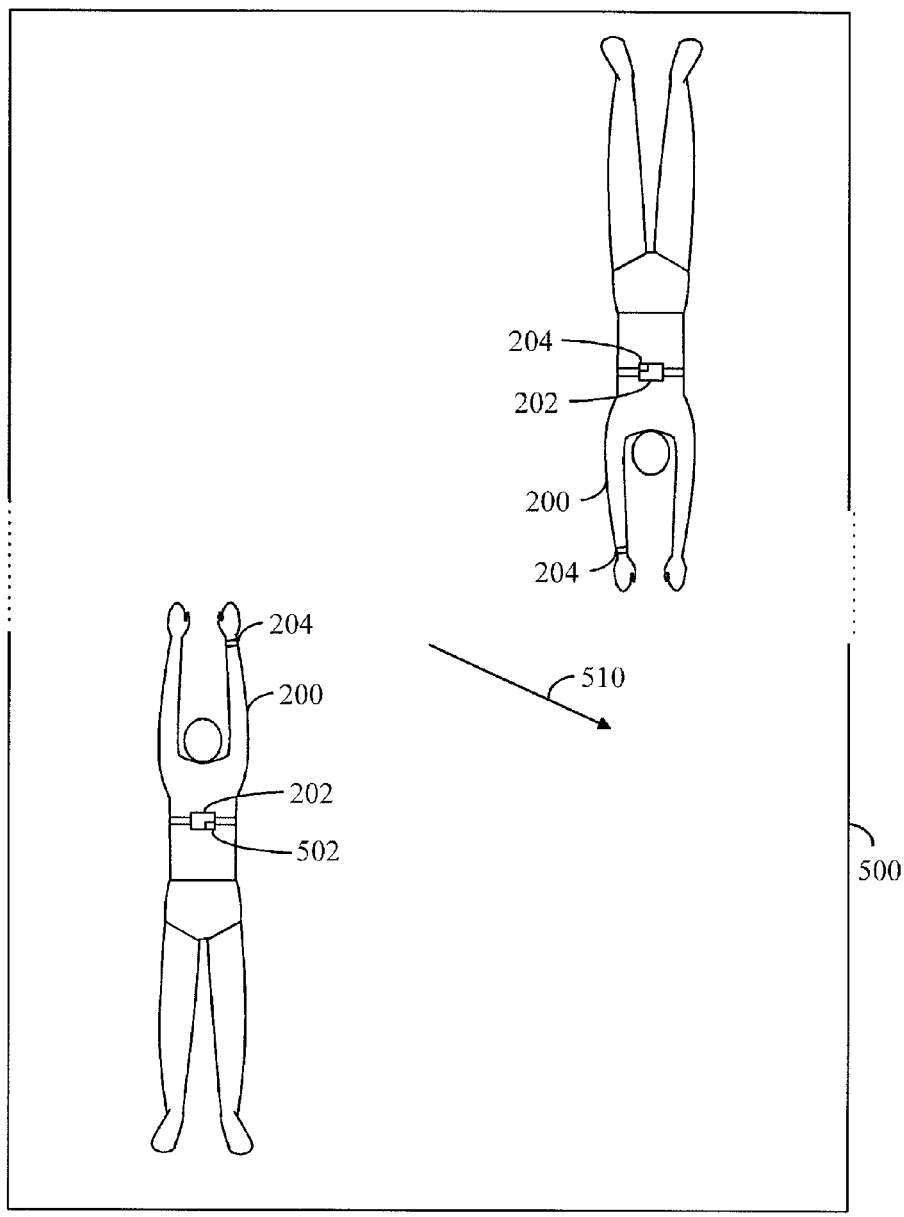
FIG. 5a shows measurement of the swimming distance.
Figure 5B:
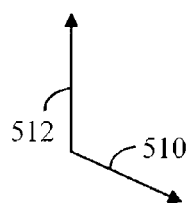
FIG. 5b shows the direction of a magnetic field when a person swims in one direction.
Figure 5C:
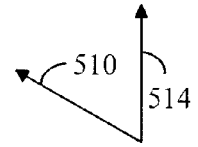
FIG. 5c shows the direction of a magnetic field when a person swims in another direction.

FIG. 5A shows a solution in which the measuring unit 102 measures for instance the swimming distance of the user 200 in a swimming pool 500. The transmitter belt 202 that is on the chest of the user in this example has an environment sensor 502 that measures the direction 510 of the magnetic field of the earth. FIG. 5B shows the direction 510 of the magnetic field in relation to a predefined direction 512 of the measuring unit 102, when the user 200 swims in one direction. The predefined direction is in this example the same as the swimming direction. FIG. 5C shows the direction 510 of the magnetic field in relation to the predefined direction 514 of the measuring unit 102, when the user swims in the other direction. The change of direction of the magnetic field is 180°, when the user moves in opposite directions. The time between two changes of direction indicates how long it takes for the user to swim from one end of the pool to the other. This way it is possible to measure the swimming time and distance, if the length of the pool is known. The measuring information can be transmitted wirelessly to a predefined communication device when it is detected that wireless data transmission is available. A corresponding solution can be used to measure the performance of the user on a running track or the like.

Figure 6:
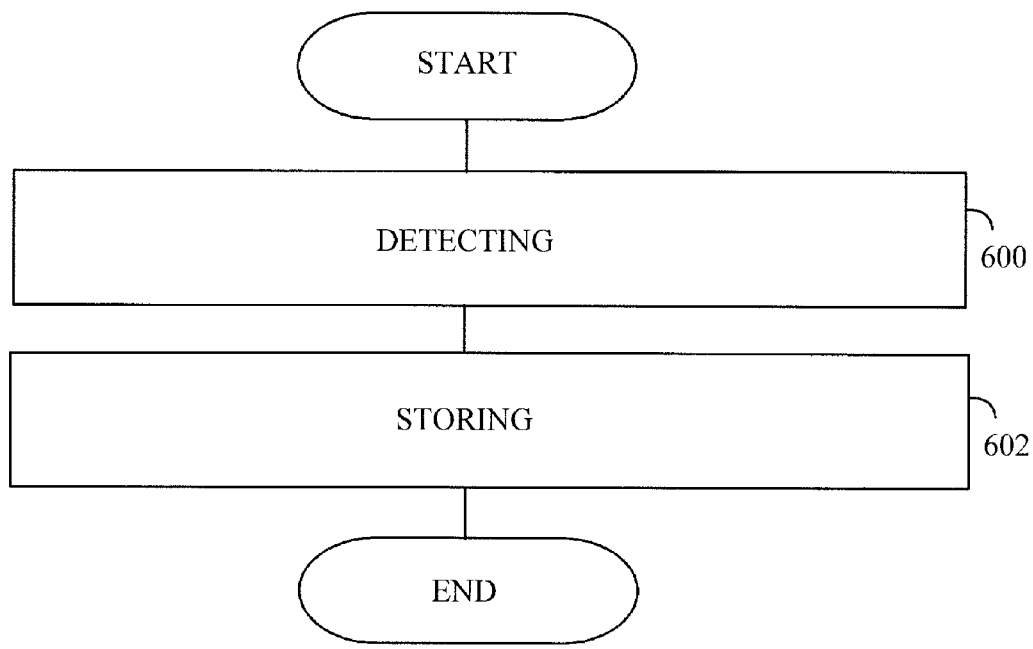
FIG. 6 shows a flow chart of the method.

FIG. 6 shows a flow chart of the method. Step 600 detects the availability of wireless data transmission in the performance transmitter. Step 602 stores measuring data into the memory of the performance transmitter, if wireless data transmission is not available, otherwise the measuring data is transmitted using wireless data transmission.

Figure 7:
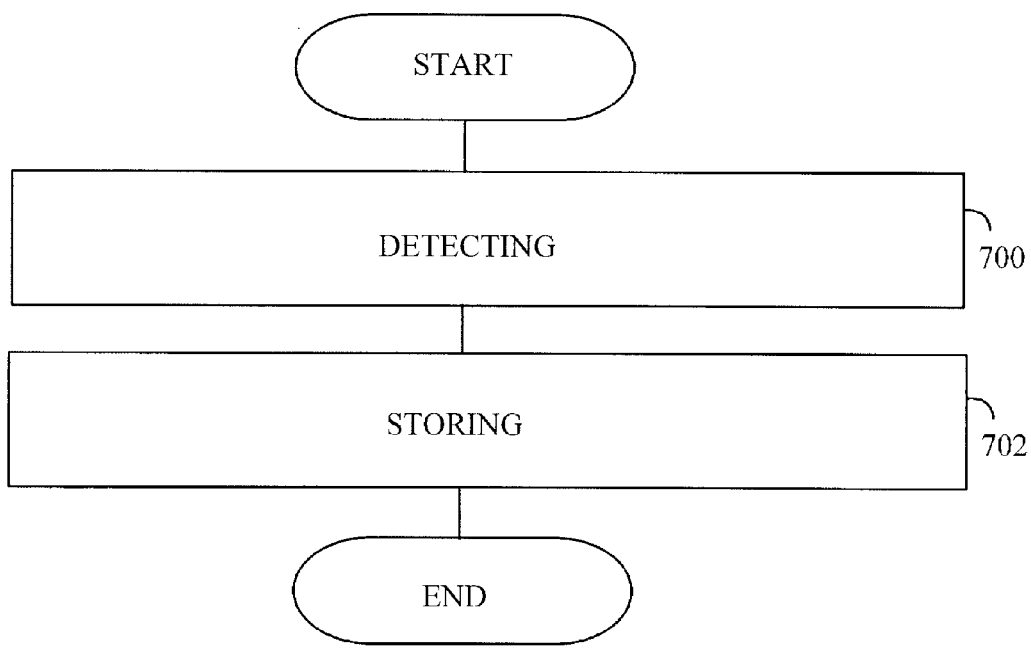
FIG. 7 shows a flow chart of the computer program.

FIG. 7 shows a flow chart of the computer program. Step 700 detects the availability of wireless transmission in the performance transmitter. Step 702 stores measuring data into the memory of the performance transmitter, if wireless data transmission is not available, otherwise the performance transmitter is controlled to transmit the measuring data by using wireless data transmission.

Even though the invention is above described with reference to the examples in the attached drawings, it is clear that the invention is not restricted to them but may be modified in many ways within the scope of the attached claims.

What is claimed is:

1. A data transmission method for use in the transmission of a performance transmitter of a portable user-specific performance monitor by using wireless data transmission that is based on radio-frequency electromagnetic radiation, the method comprising:

measuring, by the performance monitor, at least one of a movement and organ system state of the user;

detecting whether wireless data transmission capability is available in the performance transmitter by detecting that wireless data transmission capability of the performance transmitter is not available if an inhibiting command is received from a user interface of the performance transmitter when the user prevents the use of wireless data transmission or if a command that inhibits wireless data transmission is received from a predefined communication device to the performance transmitter, and by detecting that wireless data transmission of the performance transmitter is available if a permit command is received from the user interface when the user permits wireless data transmission capability from the performance transmitter or if a command that permits wireless data transmission is received from the predefined communication device to the performance transmitter, when wireless data transmission capability from the performance transmitter to the predefined communication device is available; and storing measuring data into the memory of the performance transmitter and not transmitting measuring data, if wireless data transmission capability is not available, otherwise transmitting the measuring data by using wireless data transmission.

2. A method as claimed in claim 1, the method further comprising:

detecting in the performance transmitter that wireless data transmission capability is not available in the performance transmitter, in which case measuring data is stored into the memory of the performance transmitter; and transmitting the measuring data stored into the memory of the performance transmitter through wireless data transmission after the performance transmitter has detected that wireless data transmission capability is again available.

3. A method as claimed in claim 1, wherein when transmitting measuring data through wireless data transmission from the performance transmitter, the storage of measuring data into the memory is initiated, if wireless data transmission capability from the performance transmitter becomes unavailable.

4. A method as claimed in claim 1, the method further comprising:

detecting with one or more environment sensors whether the performance transmitter is in a watery environment, and, if the performance transmitter is detected to be in a watery environment, defining that wireless data transmission capability from the performance transmitter is not available; and detecting with each environment sensor whether the performance transmitter is in air and, if the performance transmitter is detected to be in air, defining that wireless data transmission capability from the performance transmitter is available.

5. A method as claimed in claim 1, the method further comprising:

transmitting a signal to be acknowledged from the performance transmitter to a predefined communication device; and detecting that wireless data transmission capability is available, if an acknowledgement signal is received within a predefined delay from the transmission of the signal to be acknowledged; and detecting that wireless data transmission capability is not available, if no acknowledgement signal is received within a predefined delay from the transmission of the signal to be acknowledged.

6. A method as claimed in claim 1, the method further comprising compressing measuring data to be stored into the memory of the performance transmitter, when the degree of fullness of the memory exceeds a predefined threshold value.

7. A method as claimed in claim 6, the method further comprising compressing measuring data to be stored into the memory of the performance transmitter and the measuring data already in the memory.

8. A portable user-specific performance monitor comprising:

a performance transmitter, the performance transmitter being configured to measure at least one of a movement and organ system state of the user, the performance transmitter being configured to transmit measuring data wirelessly using radio-frequency electromagnetic radiation, the performance transmitter comprising a memory, the performance transmitter being configured to detect the availability of wireless transmission capability, wherein the performance transmitter is configured to receive from a user interface or predefined communication device an inhibiting command or a permit command, and on the basis of the inhibiting command it is detected that wireless data transmission capability is not available in the performance transmitter and on the basis of the permit command it is detected that wireless data transmission capability is available in the performance transmitter, the performance transmitter being configured to store into the memory of the performance transmitter measuring data and not transmitting measuring data, when the performance transmitter detects that wireless data transmission capability is not available in the performance transmitter, the performance transmitter being configured to transmit the measuring data stored into the memory of the performance transmitter, after the performance monitor detects that wireless data transmission capability is available.

9. A performance monitor as claimed in claim 8, wherein the performance transmitter is adapted to begin storing measuring data into the memory if wireless data transmission capability from the performance transmitter becomes unavailable.

10. A performance monitor as claimed in claim 8, wherein the performance monitor comprises one or more environment sensors for measuring whether the performance transmitter is in a watery environment, and the performance monitor is configured to detect that wireless data transmission capability is not available, if the performance transmitter is measured to be in a watery environment, the performance monitor being configured to detect that wireless data transmission capability is available, if the performance transmitter is measured to be in air.

11. A performance monitor as claimed in claim 8, wherein the performance transmitter is configured to transmit to a predefined communication device a signal to be acknowledged, the performance transmitter is configured to wait for an acknowledgement signal from the predefined communication device within a predefined delay from the transmission of the signal to be acknowledged and to detect that wireless data transmission capability is available, when the acknowledgement signal arrives within the predefined delay from the transmission of the signal to be acknowledged and to detect that wireless data transmission capability is not available, when the acknowledgement signal does not arrive within the predefined delay from the transmission of the signal to be acknowledged.

12. A performance monitor as claimed in claim 8, wherein the performance transmitter is configured to compress measuring data to be stored into the memory of the performance transmitter, when the degree of fullness of the memory exceeds a predefined threshold value.

13. A performance monitor as claimed in claim 12, wherein the performance transmitter is configured to compress measuring data to be stored into the memory of the performance transmitter and the measuring data already in the memory.

14. A computer program product that contains encoded instructions that when loaded into a portable user-specific performance monitor form a computer process that controls the transmission operation of a performance transmitter of a performance monitor when the performance monitor is intended to measure at least one of a movement and organ system state of the user and when the performance transmitter is intended to transmit measuring data wirelessly using radio-frequency electromagnetic radiation, the computer process comprising:

detecting the availability of wireless data transmission capability in the performance transmitter by detecting that wireless data transmission capability of the performance transmitter is not available if an inhibiting command is received from a user interface of the performance transmitter when the user prevents the use of wireless data transmission or if a command that inhibits wireless data transmission is received from a predefined communication device to the performance transmitter, and by detecting that wireless data transmission of the performance transmitter is available if a permit command is received from the user interface when the user permits wireless data transmission capability from the performance transmitter or if a command that permits wireless data transmission is received from the predefined communication device to the performance transmitter, when wireless data transmission capability from the performance transmitter to the predefined communication device is available; and storing measuring data into the memory of the performance transmitter, if wireless data transmission capability is not available, otherwise controlling the performance transmitter to transmit the measuring data by using wireless data transmission.

* * * * *